(12) United States Patent
Corbucci et al.

(10) Patent No.: US 7,158,827 B2
(45) Date of Patent: Jan. 2, 2007

(54) VENTRICULAR RATE STABILIZATION

(75) Inventors: Giorgio Corbucci, Cento (FE) (IT); Willem Boute, Dieren (NL)

(73) Assignee: Medtronic, Inc., Minneapolis, MN (US)

( * ) Notice: Subject to any disclaimer, the term of this patent is extended or adjusted under 35 U.S.C. 154(b) by 679 days.

(21) Appl. No.: 10/126,896

(22) Filed: Apr. 22, 2002

(65) Prior Publication Data
US 2003/0199935 A1    Oct. 23, 2003

(51) Int. Cl.
    *A61N 1/36* (2006.01)
(52) U.S. Cl. .......................................... 607/9
(58) Field of Classification Search ............... 607/9, 607/4, 5, 14
    See application file for complete search history.

(56) References Cited

U.S. PATENT DOCUMENTS

| | | | |
|---|---|---|---|
| 4,941,471 A * | 7/1990 | Mehra | 607/9 |
| 5,282,838 A * | 2/1994 | Hauser et al. | 607/9 |
| 5,480,413 A | 1/1996 | Greenhut et al. | |
| 5,534,016 A | 7/1996 | Boute | |
| 5,702,424 A * | 12/1997 | Legay et al. | 607/9 |
| 5,749,900 A * | 5/1998 | Schroeppel et al. | 607/4 |
| 5,749,906 A * | 5/1998 | Kieval et al. | 607/9 |
| 5,792,193 A | 8/1998 | Stoop | |
| 6,285,907 B1 | 9/2001 | Kramer et al. | |
| 6,324,427 B1 | 11/2001 | Florio | |
| 2003/0023132 A1* | 1/2003 | Melvin et al. | 600/16 |

OTHER PUBLICATIONS

Rate Stabilization by Right Ventricular Pacing in Patients With Atrial Fibrillation, PACE, vol. 9 Nov. Dec., Part II, 1986, pp. 1147-1153.

* cited by examiner

*Primary Examiner*—George R. Evanisko
*Assistant Examiner*—Michael Kahelin
(74) *Attorney, Agent, or Firm*—Daniel G. Chapik; Girma Wolde-Michael

(57) ABSTRACT

Techniques for stabilizing the rate of a ventricle, during conducted atrial fibrillation for example, adjust the escape interval of an implantable medical device to increase or decrease the pacing rate. In some embodiments, the escape interval is adjusted to achieve and maintain a percentage of pacing. In other embodiments, the stability of the ventricular rate is quantified as a function of measured R-R intervals, and the escape interval is adjusted to achieve and maintain a level of stability. In still other embodiments, a mean compensatory pause length is determined, and the escape interval is adjusted as a function of the mean compensatory pause length, to maintain the escape interval at or near the mean compensatory pause length.

14 Claims, 12 Drawing Sheets

VENTRICULAR RATE STABILIZATION

FIELD OF THE INVENTION

The present invention relates generally to cardiac pacemakers, and more particularly to cardiac pacemakers having a ventricular escape interval that can be adjusted to stabilize the ventricular rate.

BACKGROUND

When functioning properly, a heart maintains its own intrinsic rhythm, and is capable of pumping adequate blood throughout a circulatory system. This intrinsic rhythm is a function of intrinsic signals generated by the sinoatrial node, or SA node, located in the upper right atrium. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

Some patients, however, have irregular cardiac rhythms, referred to as cardiac arrhythmias. Cardiac arrhythmias result in diminished blood circulation because of diminished cardiac output. Atrial fibrillation is a common cardiac arrhythmia that reduces the pumping efficiency of the heart. Atrial fibrillation is characterized by rapid, irregular, uncoordinated depolarizations of the atria. These depolarizations may not originate from the SA node, but may instead originate from an arrhythmogenic substrate, such as an ectopic focus, within the atrial heart tissue. The reduced pumping efficiency due to atrial fibrillation requires the ventricle to work harder, which is particularly undesirable in sick patients that cannot tolerate additional stresses. As a result of atrial fibrillation, patients must typically limit activity and exercise.

An even more serious problem, however, is the risk that atrial fibrillation may induce irregular ventricular heart rhythms. Irregular atrial depolarization signals associated with atrial fibrillation are received by the AV node and may be conducted to ventricles. During atrial fibrillation, the intervals between ventricular depolarizations vary substantially. Such induced ventricular arrhythmias compromise pumping efficiency even more drastically than atrial arrhythmias and, in some instances, may be life threatening. This phenomenon is referred to as conducted atrial fibrillation, or "conducted AF."

A possible explanation for the effect of conducted atrial fibrillation on ventricular rate stability has been suggested. It has been suggested that, during atrial fibrillation, the AV node receives numerous successive stimuli originating from the atrium, and while each stimulus alone has a low amplitude which is insufficient to trigger AV node depolarization and ventricular contraction, they do cause partial depolarizations of the AV node. It has been further suggested that the effect of these partial depolarizations is cumulative, so that when a sufficient number of such stimuli are received, the AV node is depolarized resulting in unstable random ventricular contractions.

One mode of treating cardiac arrhythmias includes the use of an implantable medical device, such as a pacemaker. Pacemakers deliver timed sequences of low energy electrical stimuli, referred to as pacing pulses, to the heart. The pacing pulses cause the cardiac muscle tissue to depolarize, which in turn causes the heart to contract. By properly timing the delivery of pacing pulses, the heart can be induced to contract in proper rhythm, greatly improving its efficiency as a pump.

Wittkampf, F. H. M., et al., "Rate Stabilization by Right Ventricular Pacing in Patients with Atrial Fibrillation," PACE, Vol. 9, November-December, Part II, 1986, pp. 1147–53, disclosed that during atrial fibrillation, the ventricle can be stabilized by pacing at a rate approximately equal to the average intrinsic ventricular rate. Such therapy improves cardiac output because it stabilizes the rate of ventricular contractions to avoid short periods between contraction, which do not allow adequate ventricular filling, and long periods without a contraction, which lead to a lower average heart rate. The mechanism whereby the ventricular rate is stabilized by a pacing rate lower than the maximal intrinsic ventricular rate is not completely understood. It has been suggested that pacing the ventricles regularizes the ventricular heart rate by establishing retrograde conduction from the ventricles. This, in turn, is believed to block forward conduction of atrial signals through the AV node. As a result, irregular atrial depolarization signals do not trigger resulting irregular ventricular contractions.

In some modes of pacemaker operation, the ventricular pacing rate is defined by a ventricular escape interval. After a paced or intrinsic ventricular depolarization, the pacemaker operating in these modes senses the electrical activity within the ventricle during the escape interval, which is defined from the time of the last paced or intrinsic depolarization, and waits for an intrinsic depolarization to occur. If an intrinsic depolarization does not occur during the escape interval, the pacemaker delivers a pacing pulse.

Methods to stabilize the ventricular rate during conducted atrial fibrillation by pacing at a rate approximately equal to the average intrinsic ventricular rate are known in the art. In realization that the average intrinsic ventricular rate and the ventricular rate stability vary, some existing methods adjust the pacing rate based on changes in the intrinsic ventricular rate or the measured ventricular instability. These existing methods may adjust the pacing rate by adjusting the length of the escape interval of a pacemaker.

Some of the existing methods that adjust the pacing rate based on changes in the intrinsic ventricular rate or the measured ventricular instability, however, are susceptible to over or under pacing caused by rapid changes in the intrinsic ventricular rate. In particular, bursts of rapid intrinsic ventricular depolarizations may lead some existing methods to pace at an undesirably high a rate. Further, some of these existing methods may be slow in reaching a pacing rate that stabilizes the ventricle. Additionally, some of these existing methods may require a complex determination of the stability of the ventricular rate, which may increase the complexity, expense, and power consumption of an implantable device designed to practice the method.

The ventricular cycle length, i.e., the period between ventricular contractions, normally remains relatively constant and varies only gradually, even upon commencement of strenuous exercise. However, occasionally a premature ventricular contraction, or PVC, occurs in the form of a spurious pulse from a muscle cell which alters the normal electrical pulse pattern in the heart. Because the heart tissue does not recover from an early beat in time to conduct the next regular electrical pulse, the subsequent normal heartbeat does not occur. This phenomenon may also be caused by retrograde conduction of the PVC to the AV node, which increases the conduction time of the next regular electrical pulse from the atria. This longer than normal period between ventricular contractions caused by a PVC is referred to as the compensatory pause.

Another existing method for stabilizing the ventricular rate discloses that the length of a compensatory pause can be used as an indicator of the optimal pacing rate for ventricular rate stabilization. Mazzocca, et al., "The Compensatory Pause (CP) of Atrial Fibrillation (AF): A Marker for Ventricular Rate Stabilisation (VRS) in Patients (PTS) with Chronic AF (CAF)," Europace Supplements, Vol. 2, January 2001, p. 21, discloses that the length of a compensatory pause may be measured as the interval between a paced ventricular depolarization and an intrinsic ventricular depolarization. Mazzocca, et al. discloses measuring the length of several compensatory pauses to determine a mean compensatory pause length, and pacing at the rate corresponding to the mean compensatory pause length to stabilize the ventricular rate without significantly increasing the mean ventricular rate.

One existing method to further distinguish paced ventricular depolarizations from intrinsic ventricular depolarizations involves distinguishing between a true paced depolarization and a fusion beat. A fusion beat was not caused by the pacing pulse, but was instead an intrinsic ventricular depolarization that occurred nearly simultaneously with the delivery of the pacing pulse. Fusion beats can result in magnification, diminishment or abolition of the R-wave of the sensed voltage signal. Existing methods determine whether a particular heart depolarization is the result of a fusion beat by examining the T-wave generated during the cardiac cycle containing the particular heart depolarization. A T-wave represents the repolarization of the ventricular tissue and always follows a depolarization of the ventricular tissue. For example, U.S. Pat. No. 5,534,016, issued to Boute, discloses measuring the amplitude of a T-wave to determine whether a particular depolarization was the result of a fusion beat.

Examples of the above referenced existing techniques and/or devices for stabilizing the ventricular rate and for detecting fusion beats may be found in the issued U.S. Patents listed in Table 1 below.

TABLE 1

| Pat. No. | Inventor | Issue Date |
| --- | --- | --- |
| 6,324,427 | Florio | Nov. 27, 2001 |
| 6,285,907 | Kramer et al. | Sep. 4, 2001 |
| 5,792,193 | Stoop | Aug. 11, 1998 |
| 5,534,016 | Boute | Jul. 9, 1996 |
| 5,480,413 | Greenhut et al. | Jan. 2, 1996 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to stabilization of the ventricular rate utilizing a pacemaker. Such problems may include susceptibility to over or under pacing, inability to quickly reach a pacing rate that stabilizes the ventricles, or complexity of the determination of the stability of the ventricular rate. Such problems may also include inability to adjust the pacing rate as a function of variations in the mean compensatory pause length and the inability to discriminate between a true compensatory pause, which occurs between a paced ventricular depolarization and an intrinsic ventricular depolarization, and an interval between a fusion beat and an intrinsic ventricular depolarization.

Therefore, it is an object of the present invention to provide an implantable medical device and method to stabilize the ventricular rate that is less susceptible to over or under pacing, that more quickly reaches a pacing rate that stabilizes the ventricle, and requires a less complex determination of the stability of the ventricular rate than existing devices and methods. It is a further object of the present invention to provide an implantable medical device and method capable of continuously adjusting the pacing rate as a function of variations in the mean compensatory pause length and discriminating between true compensatory pauses and intervals between fusion beats and intrinsic ventricular depolarizations. In particular, it is an object of the present invention to provide an implantable medical device and system that stabilizes the ventricular rate by achieving and maintaining a percentage of paced pulses, by quantifying the stability of the ventricular rate as a function of measured R-R intervals and a range of rates and adjusting the escape interval to maintain a level of stability, or by maintaining the escape interval at or near a target length determined as a function of the measured lengths of compensatory pauses.

The present invention has certain features. Various embodiments of the implantable medical device of the present invention may feature, for example, electrodes to deliver pacing pulses to and sense electrical activity within a ventricle of a heart, and a microprocessor that detects the occurrence of depolarizations of the ventricle as a function of the electrical activity within the ventricle. In various embodiments, the microprocessor executes software-based algorithms in order to control pacing circuitry stabilize the ventricular rate. For example, the microprocessor may adjust the pacing rate by adjusting an escape interval.

In some embodiments, the microprocessor may determine whether depolarizations of the ventricle were caused by the delivery of pacing pulses, and adjust an escape interval to achieve and maintain a percentage of paced depolarizations which stabilizes the ventricular rate.

In added embodiments, the microprocessor may measure R-R intervals for detected depolarizations. In addition, the microprocessor may quantify the stability of the ventricular rate as a function of the measured R-R intervals and a rate range, and adjust the escape interval to achieve and maintain a level of stability.

In further embodiments, the microprocessor identifies compensatory pauses among detected depolarizations by identifying intrinsic depolarizations that are preceded by depolarizations caused by pacing pulses. For example, the microprocessor may distinguish between depolarizations caused by pacing pulses and fusion beats by analyzing the T-waves associated with the depolarizations. The microprocessor may measure compensatory pauses by measuring R-R intervals associated with the intrinsic depolarizations, and adjust the escape interval to maintain the escape interval at or near an average length of measured compensatory pauses.

Various embodiments of the implantable medical device of the present invention also may feature an input/output circuit to allow a physician to program parameters of algorithms utilized by the microprocessor to stabilize the ventricular rate.

The present invention has certain advantages. That is, in comparison with prior art devices and methods to stabilize the ventricular rate, various features of the present invention described above provide certain advantages. For example, by considering a plurality of depolarizations when deciding whether to adjust the escape interval, the present invention may avoid over or under pacing, and may more quickly achieve a pacing rate that stabilizes the ventricle. Further, by adjusting the escape interval as a function of the variations in the mean compensatory pause length and identifying true compensatory pauses, the present invention more completely takes advantage of the benefit of pacing at or near the rate indicated by a compensatory pause, which is a stable ventricular rate with little change in the mean ventricular rate. Additionally, the present invention allows a physician greater control of the rate stabilization, by allowing the physician to program parameters of the rate stabilization algorithms.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
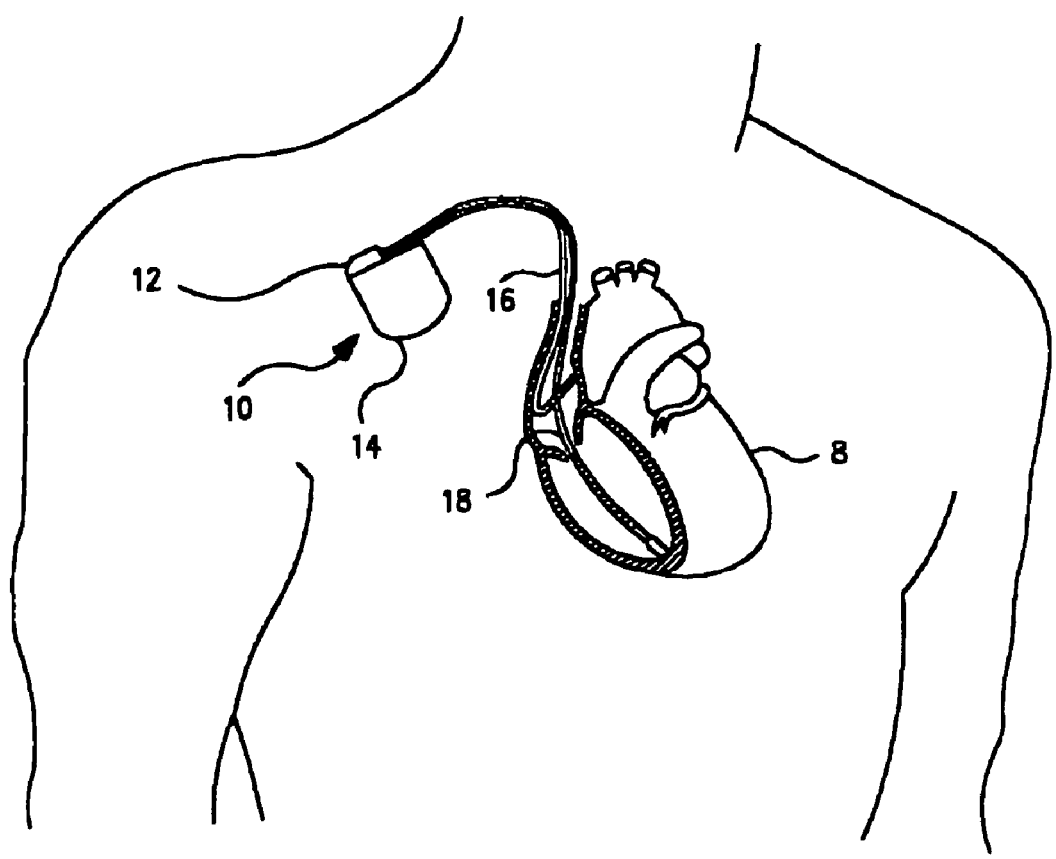
FIG. 1 is a schematic view of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and repolarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
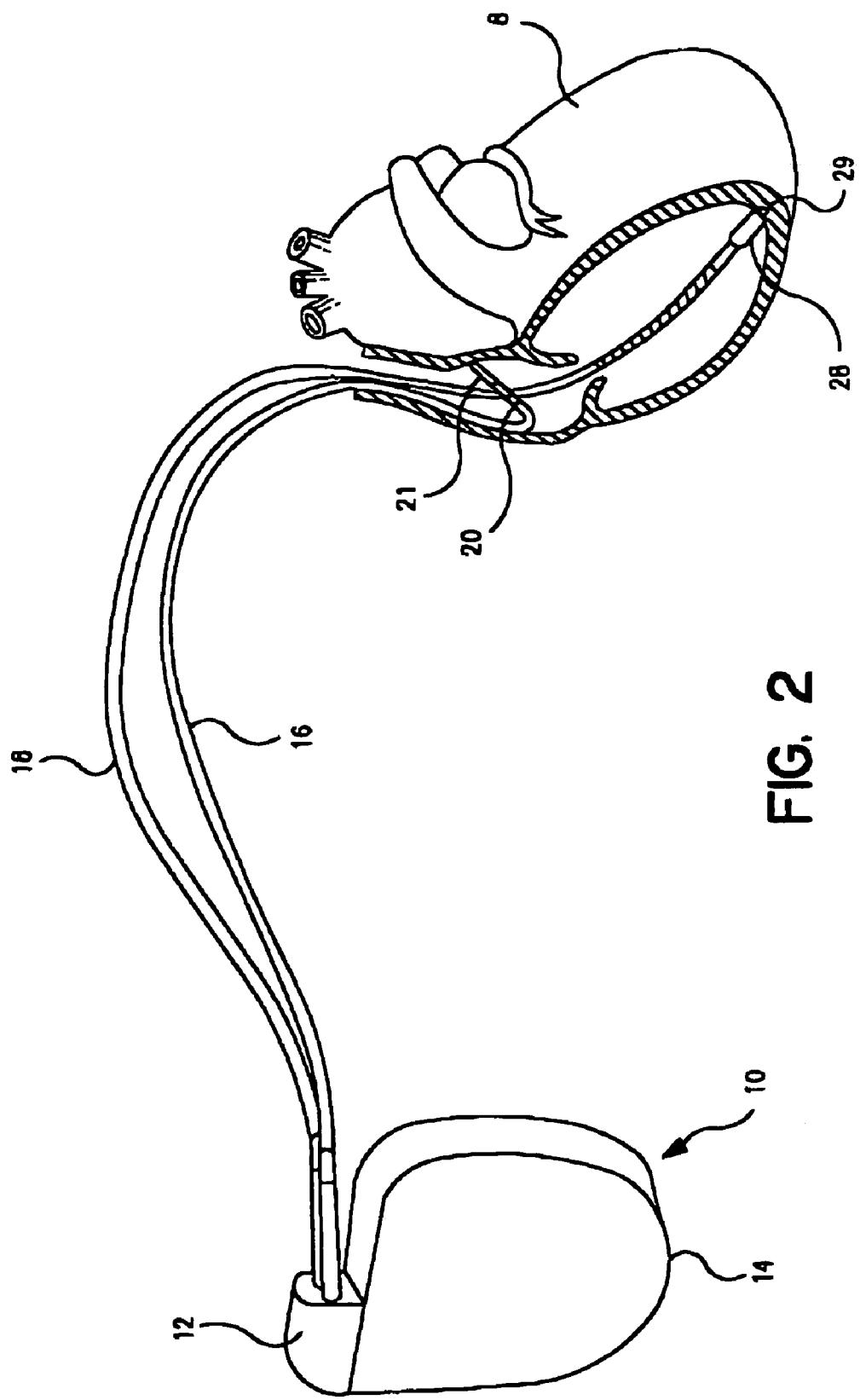
FIG. 2 shows the implantable medical device of FIG. 1 located in and near a heart.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
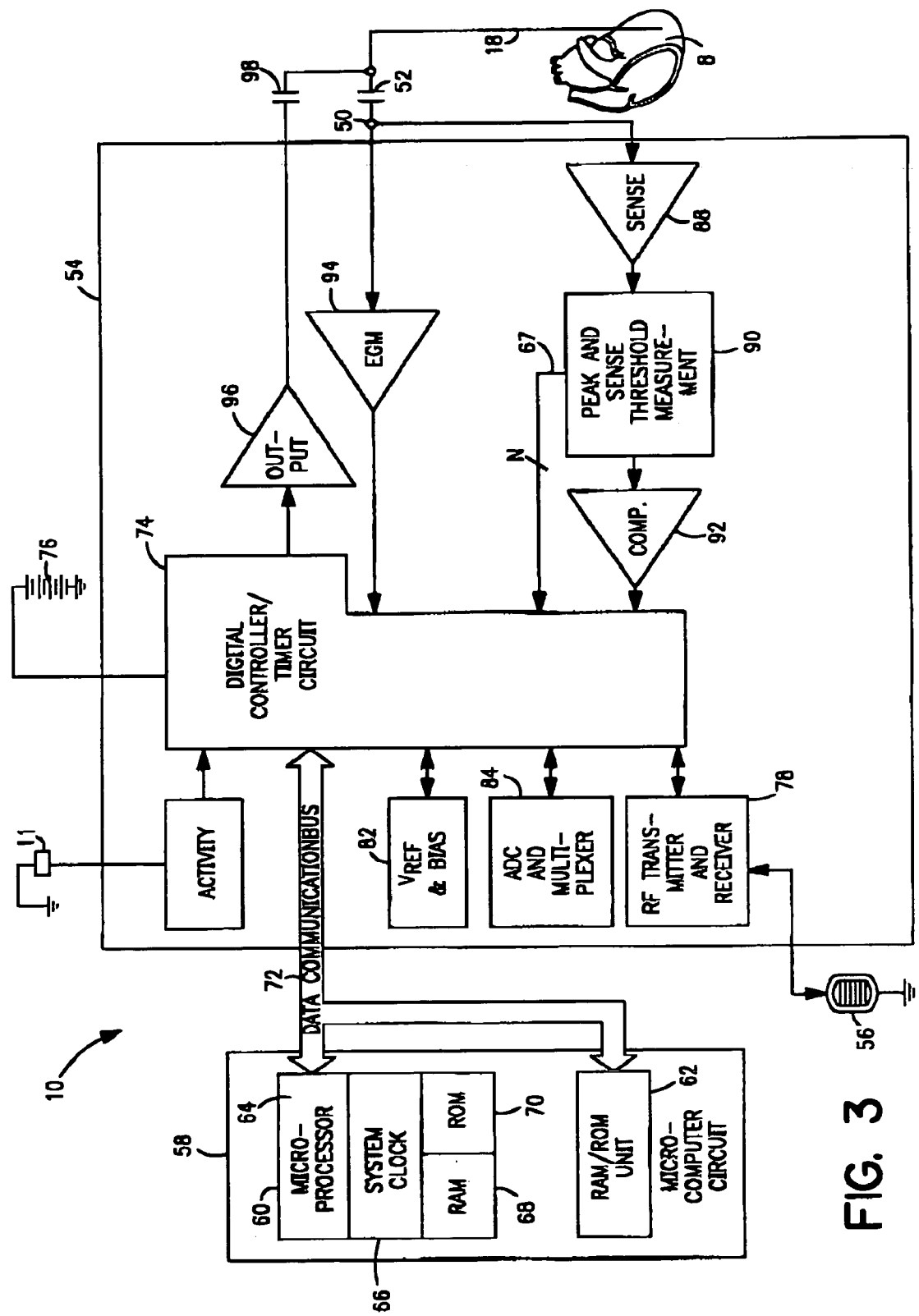
FIG. 3 is a block diagram illustrating the constituent components of an implantable medical device as shown in FIG. 1.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However, it is understood that similar circuitry and connections not explicitly shown in FIG. 3 apply to lead 16 (shown in FIGS. 1 and 2).

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Microprocessor 64 may be implemented as an embedded microprocessor, controller, and the like, or as an ASIC, FPGA, discrete logic circuitry, or analog circuitry. Microprocessor 64 may execute instructions stored in any computer-readable medium suitable for storing instructions including on-board RAM 68, ROM 70, off-board circuit 62, non-volatile random access memory (NVRAM) (not shown), electrically erasable programmable read-only memory (EEPROM) (not shown), flash memory (not shown), and the like.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

In the practice of the present invention, microprocessor 64 may execute software-implemented algorithms stored in memory, such as on-board RAM 68, ROM 70, or off-board circuit 62 of microcomputer circuit 58, to adjust the ventricular escape interval of IMD 10 in order to stabilize the ventricular rate as will be described in more detail below. These algorithms may be executed in response to detected ventricular rate instability. For example, these algorithms may be executed in response to detected atrial fibrillation that is conducted to the ventricles. In cases of chronic ventricular rate instability, such as ventricular rate instability caused by conducted chronic atrial fibrillation, the algorithms may operate continuously. In cases of periodic ventricular rate instability, such as ventricular rate instability caused by conducted paroxysmal atrial fibrillation, the algorithms may be activated in response to the detected ventricular rate instability or atrial fibrillation. Ventricular rate instability or atrial fibrillation may be detected by any of the methods described below. Microprocessor 64 may communicate the adjusted escape interval to digital controller/timer circuit 74 via data communications bus 72.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

Sense amplifier 88, peak sense and threshold measurement unit 90 and comparator/threshold detector 92 may be used in the practice of the present invention to detect the occurrence of ventricular depolarizations by detecting R-waves in the signal received from lead 18. Microprocessor 64 may receive a signal indicating the occurrence of a ventricular depolarization via digital controller/timer circuit 74 and data communications bus 72, and may use the indication in the execution of the software-implemented algorithms mentioned above.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Additionally, ADC and multiplexer unit 84 may digitize the electrogram signal received by digital controller/timer circuit 74, and the digitized electrogram signal may be received by microprocessor 64 via data communications bus 72. Microprocessor 64 may process the digitized electrogram signal in order to analyze T-waves within the signal to detect the occurrence of fusion beats as will be described in more detail below.

Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

During pacing, a ventricular escape interval counter within digital controller/timer circuit 74 is reset upon sensing of R-waves as indicated by signals received from sense amplifier 88, peak sense and threshold measurement unit 90 and comparator/threshold detector 92, and in accordance with the selected mode of pacing on time-out triggers generation of pacing pulses by output pulse generator 96, which is coupled to electrodes 28 and 29. The ventricular escape interval counter is also reset on generation of pacing pulses. The duration of the ventricular escape interval defined by the ventricular escape interval timer is determined by microprocessor 64 via data communications bus 72.

Microprocessor 64 may receive a signal indicating that a pacing pulse has been delivered to the ventricle from digital controller/timer circuit 74 in addition to the signal indicating that an R-wave has occurred, and may thus determine whether a particular ventricular depolarization is the result of a pacing pulse. If a ventricular blanking interval is employed, microprocessor 64 may use this pacing pulse delivery signal to detect the occurrences of the paced ventricular depolarizations.

Microprocessor 64 may measure an R-R interval by measuring the time period between R-wave occurrence signals received from digital controller/timer circuit 74. If a ventricular blanking period is employed, microprocessor 64 may measure R-R intervals by measuring the time period between R-wave occurrence signals, pacing pulse delivery signals, or both. Additionally, the value of the count present in the ventricular escape interval counter when reset by a detected R-wave or a pacing pulse delivery may be used by microprocessor 64 to measure an R-R interval.

Microprocessor 64 may adjust the escape interval as a function of the above determinations or measurements as will be described in more detail below.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, VDD, DDI and VVI modes. In other preferred embodiments of the present invention, IMD 10 may operate in various rate-responsive modes, including, but not limited to, DDDR, VDDR, DDIR and VVIR modes. Some embodiments of the present invention are capable of operating in both non-rate-responsive and rate-responsive modes. In particular, IMD 10 of present invention operates in modes wherein the delivery of a pulse to the ventricle is inhibited when an intrinsic ventricular depolarization is sensed.

When used in cases of chronic ventricular rate instability, such as ventricular rate instability cause by conducted chronic atrial fibrillation, IMD 10 may continuously operate in a rate responsive mode wherein the ventricular pacing rate is not coupled to the sensed or paced atrial rate, such as VVIR. When used in cases of periodic ventricular instability, such as ventricular rate instability caused by conducted paroxysmal atrial fibrillation, IMD 10 may, in the absence of ventricular rate instability or atrial fibrillation, operate in various non-rate-responsive and/or dual chamber modes wherein the ventricular pacing rate is coupled to the sensed or paced atrial rate. When ventricular rate instability or atrial fibrillation is detected, however, these embodiments of IMD 10 may be configured to switch to a rate responsive mode wherein the ventricular pacing rate is not coupled to the sensed or paced atrial rate, such as VVIR.

In various embodiments of the present invention, IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
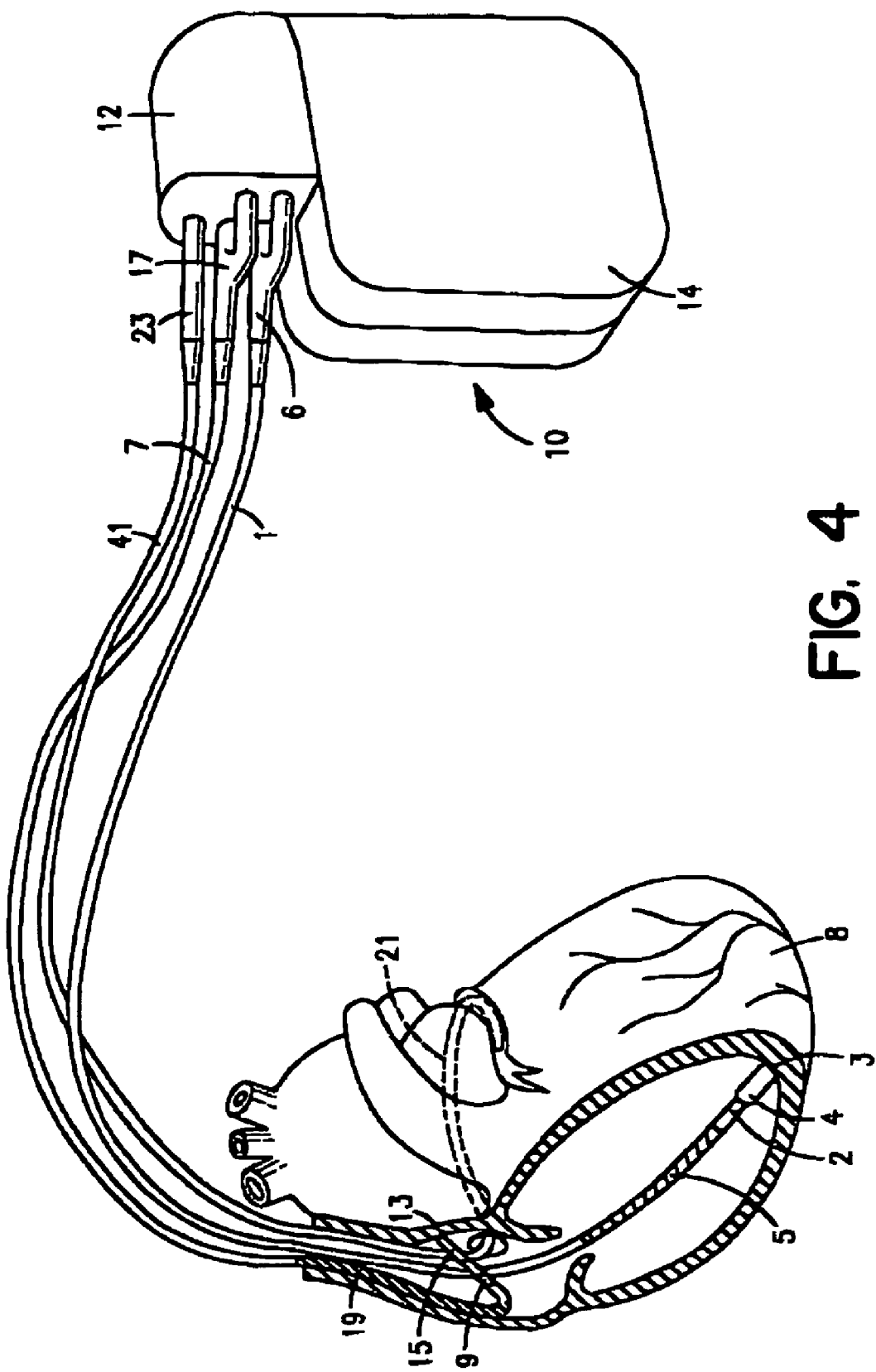
FIG. 4 shows a pacemaker-cardioverter-defibrillator located in and near a heart.
Figure 5:
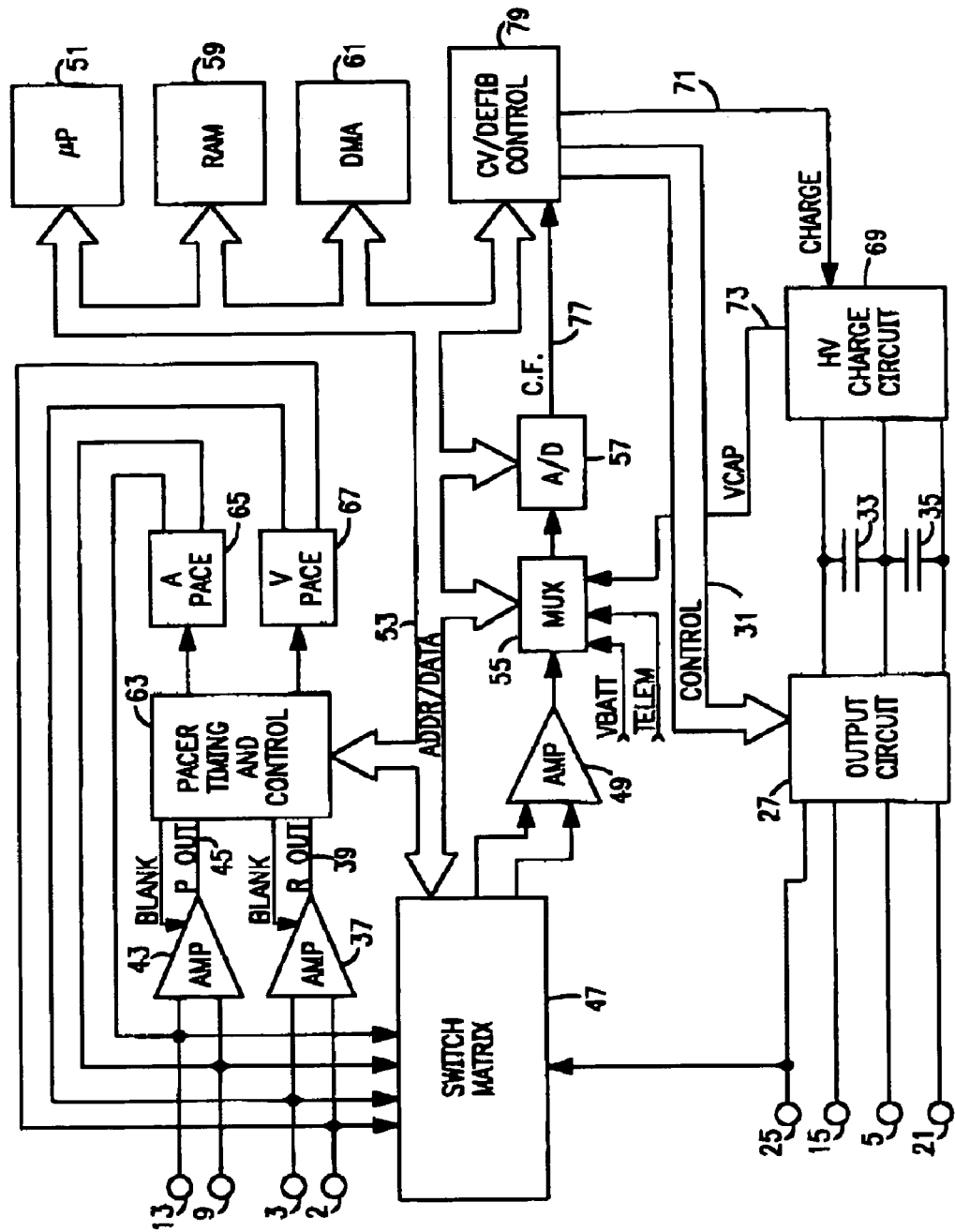
FIG. 5 is a functional schematic diagram of one embodiment of an implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing electrical activity within the ventricle. At the proximal end of the lead is bifurcated connector 6 which carries three electrical connectors, each coupled to one of the coiled conductors. Elongated coil electrode 5, which is a defibrillation electrode 5, may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing electrical activity within the atrium. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. Elongated coil defibrillation electrode 41 may be about 5 cm in length.

IMD 10 is shown in FIG. 4 in combination with leads 1, 7 and 41, and lead connector assemblies 23, 17 and 6 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of IMD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of a capacitor bank (which includes capacitors 33 and 35) during delivery of defibrillation pulses.

Electrodes 2 and 3 are located on or in the ventricle of the patient and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold. R-wave amplifier 37 may be used in the practice of the present invention to detect the occurrence of ventricular depolarizations, by detecting R-waves in the signal received from lead 1. Mircroprocessor 51 may receive a signal indicating the occurrence of a ventricular depolarization via pacer timing and control circuit 63 and address/data bus 53.

Electrodes 9 and 13 are located on or in the atrium of the patient and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824 to Keimel et al., hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art. Microprocessor 51 may process the digitized signals in order to analyze T-waves within the signals to detect the occurrence of fusion beats as will be described in more detail below.

Microprocessor 64 may be implemented as an embedded microprocessor, controller, and the like, or as an ASIC, FPGA, discrete logic circuitry, or analog circuitry. Microprocessor 64 may execute instructions stored memory 59, which may comprise any computer-readable medium suitable for storing instructions including random access memory (RAM), read-only memory (ROM) non-volatile random access memory (NVRAM), electrically erasable programmable read-only memory (EEPROM), flash memory, and the like.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art. Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

Microprocessor 51 may execute software-implemented algorithms stored in memory 59 to adjust the ventricular escape interval of IMD 10 in order to stabilize the ventricular rate as will be described in more detail below. These algorithms may be executed in response to detected ventricular rate instability. For example, these algorithms may be executed in response to detected atrial fibrillation that is conducted to the ventricles. In cases of chronic ventricular rate instability, such as ventricular rate instability caused by chronic atrial fibrillation that is conducted to the ventricles, the algorithms may operate continuously. In cases of periodic ventricular rate instability, such ventricular rate instability that is caused by paroxysmal atrial fibrillation that is conducted to the ventricles, the algorithms may be activated in response to the detected ventricular rate instability or atrial fibrillation. Ventricular rate instability or atrial fibrillation may be detected by any of the methods described below. The adjusted escape interval may be communicated to pacing circuitry 63 via address/data bus 53. Additionally, microprocessor 51 may use the R-wave occurrences signals received from pacer timing and control circuit 63 in the execution of the software-implemented algorithms.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Microprocessor 51 may receive a signal indicating that a pacing pulse has been delivered to the ventricle from pacer timing and control circuit 63 in addition to the signal indicating that an R-wave has occurred, and may thus determine whether a particular ventricular depolarization is the result of a pacing pulse. If a ventricular blanking interval is employed, microprocessor 51 may use this pacing pulse delivery signal to detect the occurrences of the paced ventricular depolarizations.

Microprocessor 51 may measure an R-R interval by measuring the time period between R-wave occurrence signals received from pacer timing and control circuit 63. If a ventricular blanking period is employed, microprocessor 51 may measure R-R intervals by measuring the time period between R-wave occurrence signals, pacing pulse delivery signals, or both. Additionally, the value of the count present in a ventricular escape interval counter when reset by a detected R-wave or a pacing pulse delivery may be used by microprocessor 51 to measure an R-R interval.

Microprocessor 51 may adjust the escape interval as a function of the above determinations or measurements as will be described in more detail below.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Exemplary techniques for stabilizing a ventricular rate utilizing IMD 10 are described in greater detail with reference to the Figures that follow. For the sake of clarity, the components of IMD 10 identified in the description that follows are limited to those of the embodiment of IMD 10 described in FIGS. 1–3. It is understood that components of the embodiment of IMD 10 described in FIGS. 4 and 5, or other equivalent components, may perform the functions described, and are within the scope of the present invention.

Figure 6:
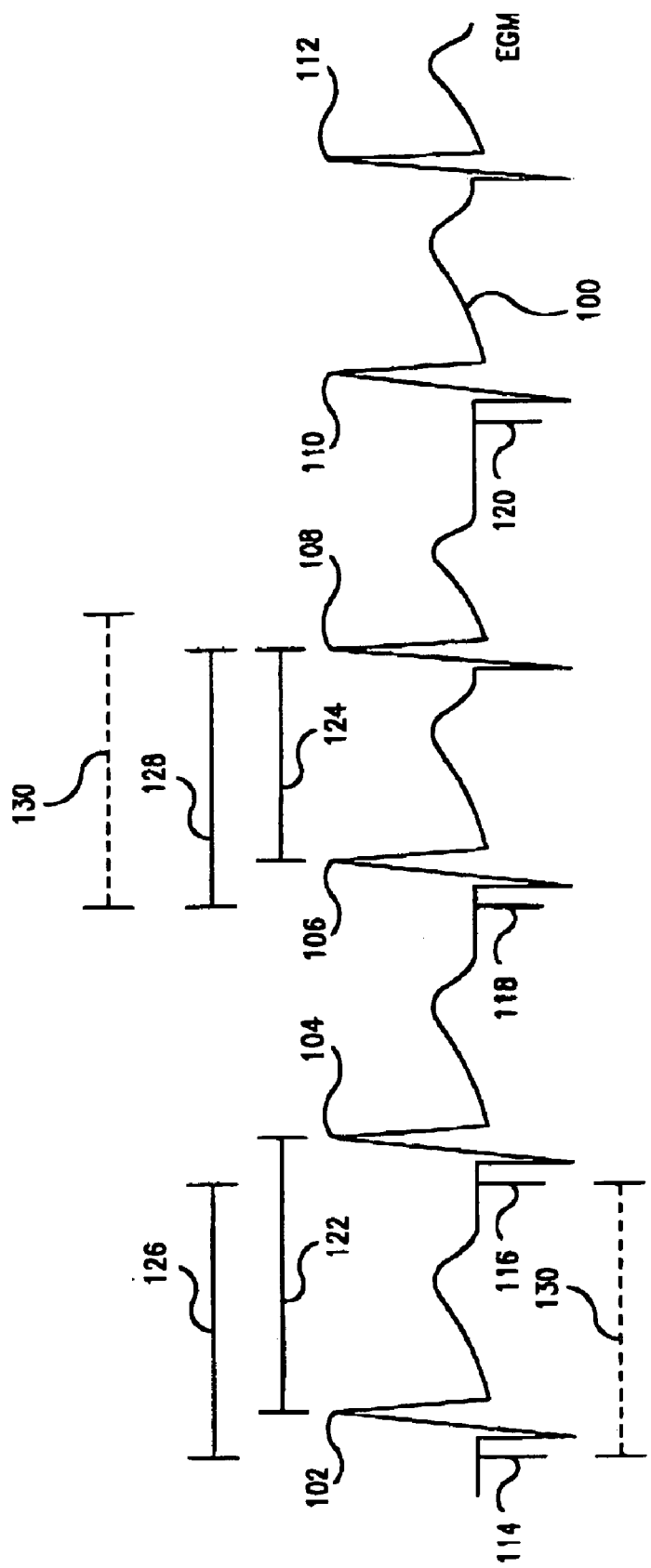
FIG. 6 is a timing diagram providing an overview of exemplary modes of operation of an implantable medical device to stabilize a ventricular rate, either by maintaining a percentage of paced depolarizations, or as a function of measured R-R interval lengths.

FIG. 6 is a timing diagram providing an overview of exemplary modes of operation of IMD 10 to stabilize a ventricular rate, either by maintaining a percentage of paced depolarizations, or as a function of measured R-R interval lengths. In particular, the timing diagram is useful to illustrate techniques employed by IMD 10 to detect the occurrence of a ventricular depolarization, and to either determine whether the ventricular depolarization was caused by a pacing pulse, or to measure the R-R interval for the ventricular depolarization.

EGM signal 100 represents a signal received from electrodes 28 and 29 on lead 18 of IMD 10. EGM signal 100 represents the electrical activity sensed by electrodes 28 and 29 within a ventricle of heart 8. R-waves 102–112 of EGM signal 100, which represent depolarizations of the ventricle, are shown. As can be seen, pacing pulses 114–120, which are also shown on EGM signal 100, were delivered prior to the depolarizations represented by R-waves 102, 104, 106 and 110. Thus, pacing pulses 114–120 caused the depolarizations represented by R-waves 102, 104, 106 and 110.

Sense amplifier 88, peak sense and threshold measurement unit 90 and comparator/threshold detector 92 may be used to detect the occurrence of ventricular depolarizations by detecting R-waves 102–112 in EGM signal 100. Microprocessor 64 may receive a signal when each of R-waves 102–112 in EGM signal 100 is detected. Microprocessor 64 may receive these R-wave occurrence signals via digital controller/timer circuit 74 and data communications bus 72.

Microprocessor 64 may also receive a signal when each of pacing pulses 114–120 is delivered by output pulse generator 96. Digital controller/timer circuit 74 controls the delivery of pacing pulses by output pulse generator 96. Microprocessor 64 may receive these pacing pulse delivery signals from digital controller/timer circuit 74 via data communications bus 72. By determining whether a pacing pulse delivery signal was received before an R-wave occurrence signal, microprocessor 64 may determine whether the ventricular depolarization represented by the R-wave was caused by a pacing pulse.

A ventricular refractory period is a period of time immediately following the delivery of a pacing pulse to a ventricle, during which no sensing within the ventricle occurs.

In embodiments of IMD 10 that utilize a ventricular refractory period, sense amplifier 88, peak sense and threshold measurement unit 90 and comparator/threshold detector 92 may not detect the occurrence of R-waves, such as R-waves 102, 104, 106 and 110, which are caused by the delivery of a pacing pulse, such as pacing pulses 114–120. In such embodiments, microprocessor 64 may rely solely on the pacing pulse delivery signals to detect paced depolarizations, and to determine the times at which the paced depolarizations occurred.

Microprocessor 64 may also measure an R-R interval, such as exemplary R-R intervals 122 and 124, for each of R-waves 102–112. An R-R interval represents the time between occurrences of R-waves in an EGM signal, and thus the time between ventricular depolarizations. The R-R interval for a particular R-wave is measured as the interval between the particular R-wave and the R-wave that preceded it. Thus, R-R interval 122, for example, is associated with R-wave 104. Microprocessor 64 may measure R-R interval 122 by measuring the length of time between the time microprocessor 64 received the signal indicating that the occurrence of R-wave 102 was detected, and the time microprocessor 64 received the signal indicating that the occurrence of R-wave 104 was detected.

In embodiments of IMD 10 that utilize a ventricular refractory period, R-R intervals will either be measured from the delivery of a pacing pulse, or the occurrence of an R-wave that represents an intrinsic ventricular contraction, as illustrated by R-R intervals 126 and 128. R-R interval 126, which is associated with paced depolarization R-wave 104, may be measured from the time of pacing pulse 114 to the time of pacing pulse 116. R-R interval 128, which is associated with intrinsic depolarization R-wave 108, on the other hand, is measured from the time of pacing pulse 118 to the time microprocessor 64 received the signal indicating that the occurrence of R-wave 108 was detected.

FIG. 6 also illustrates the function of escape interval 130. After digital controller/timer circuit 74 controls output pulse generator 96 to deliver pacing pulse 114, circuit 74 may activate an escape interval counter. In this example, the escape interval counter reaches a value equivalent to the length of escape interval 130 before digital controller/timer circuit 74 receives another R-wave occurrence signal from sense amplifier 88, peak sense and threshold measurement unit 90 and comparator/threshold detector 92. When the escape interval counter reaches the escape interval value, digital controller/timer circuit 74 controls output pulse generator 96 to deliver pacing pulse 116 and resets the escape interval counter.

As can be seen in FIG. 6, the length of escape interval 130 is greater than R-R interval 128. Thus the depolarization associated with R-wave 108 occurs before the escape interval counter reaches the escape interval value. When digital controller/timer circuit 74 receives the signal from sense amplifier 88, peak sense and threshold measurement unit 90 and comparator/threshold detector 92 indicating that R-wave 108 has occurred in EGM signal 100, circuit 74 resets the escape interval counter without controlling output pulse generator 96 to deliver a pacing pulse. The length of escape interval 130 may be set by microprocessor 64.

In addition to the above-discussed methods by which microprocessor 64 may measure R-R interval lengths, microprocessor 64 may alternatively measure an R-R interval length as a function of the value of the escape interval counter before it is reset by an intrinsic R-wave occurrence or a time-out and pacing pulse delivery. The value of the escape interval counter may be received from digital controller/timer circuit 74 with each R-wave occurrence signal or pacing pulse delivery signal.

Figure 7:
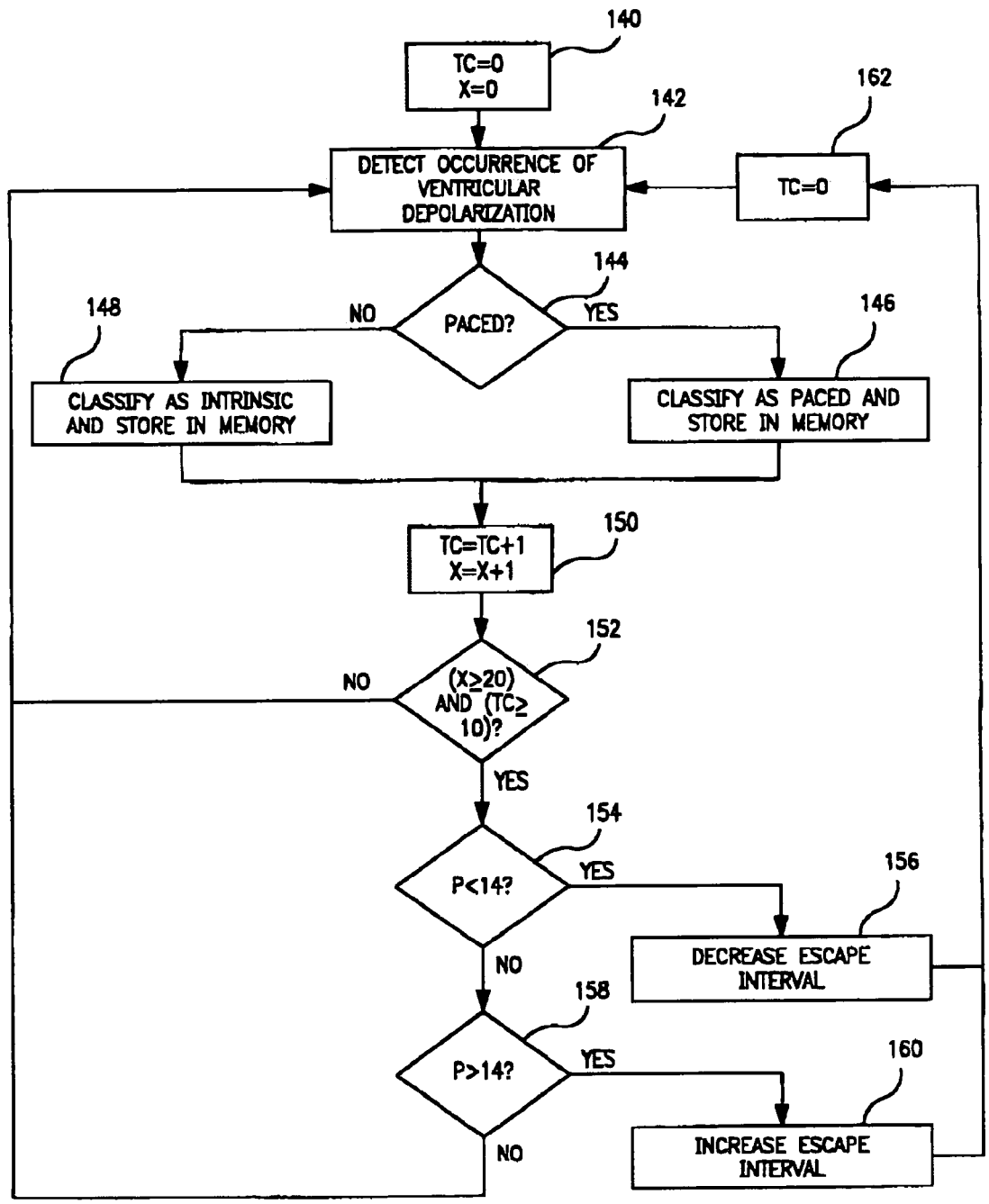
FIG. 7 is a flow diagram further illustrating the operation of an implantable medical device to stabilize the ventricular rate by maintaining a percentage of paced depolarizations.

FIG. 7 is a flow diagram further illustrating the operation of IMD 10 to stabilize the ventricular rate by achieving and maintaining a percentage of paced depolarizations. In particular, the flow diagram illustrates one embodiment of a ventricular rate stabilization algorithm that may be executed by microprocessor 64, which stabilizes the ventricular rate by achieving and maintaining a percentage of paced depolarizations. This algorithm may be executed, for example, during conducted atrial fibrillation.

In this exemplary embodiment, the target value for the percentage of paced depolarizations is set at seventy percent. Any percentage target value may be used, although it has been found that paced percentages substantially above seventy percent may result in a significant and undesirable increase in the mean heart rate, while paced percentages substantially below seventy percent may not adequately stabilize the ventricle. Generally, paced percentages within the range from sixty to eighty percent are preferred.

In this embodiment, microprocessor 64 may determine whether and how to adjust the escape interval based on the percentage of paced depolarizations among a number of the most recently detected deopolarizations. The number of depolarizations considered may, for example, be twenty as shown in FIG. 7. Again, any number of depolarizations may be considered. However, the greater the number of depolarizations considered, the more resistant this ventricular rate stabilization algorithm is to overpacing caused by bursts of rapid ventricular depolarizations.

In a further effort to avoid overpacing, this embodiment of the ventricular rate stabilization algorithm may wait for ten or more cardiac cycles after varying the escape interval before again evaluating the most recent twenty depolarizations. Thus, this embodiment of the ventricular rate stabilization algorithm guarantees at least ten cardiac cycles occur between rate variations. This wait period is referred to as the time constant after the variation of the pacing rate, and may also be set at any value.

The target percentage, number of depolarizations considered, and the value of the time constant may be included in loaded software, or selected by a physician. The physician may select the values of these parameters using an external programming unit and/or RF transmitter and receiver telemetry unit 78. These values may be stored in at least one of RAM 68, or off-board circuit 62.

When the ventricular rate stabilization algorithm is initiated, it will need to evaluate a minimum number cardiac cycles, e.g., twenty cycles, before it can make its first determination of the percentage of paced depolarizations among a number of the most recent depolarizations. Thus, the value of an initialization iteration counter variable, X, is intitially set at zero (140). The value of a time constant counter variable, TC, is also initially set to zero. The value of the escape interval may, for example, initially be set to a value corresponding to the minimum allowed pacing rate.

Each time that microprocessor 64 detects the occurrence of a ventricular depolarization (142), it determines whether the depolarization was caused by a pacing pulse (144). Microprocessor 64 may detect the occurrence of a ventricular depolarization and determine whether it was caused by a pacing pulse using any of the above-described methods. If microprocessor 64 determines that the ventricular depolarization was caused by a pacing pulse, it may classify the depolarization as paced and store an indication that the depolarization was paced in memory (146), such as RAM 68 or off-board circuit 62. If microprocessor 64 does not determine that the ventricular depolarization was caused by a pacing pulse, it may classify the depolarization as intrinsic and store an indication that the depolarization was intrinsic in memory (148).

Each time microprocessor 64 classifies a depolarization, the values of X and TC are incremented by one (150). Until the value of X equals or exceeds twenty and the value of TC equals or exceeds ten, microprocessor 64 may not proceed to determine the percentage of paced depolarizations among the most recently detected twenty depolarizations (152). Thus, during the initialization period, microprocessor 64 is directed to detect and classify twenty depolarizations before any determination or escape interval adjustment is made.

After an adequate number of depolarizations have been detected and classified, in this case twenty, microprocessor 64 proceeds to compare the percentage of paced depolarizations to the target percentage. Microprocessor 64 may make this comparison, as illustrated in this embodiment, by comparing the number of depolarizations caused by pacing pulses among the most recent twenty depolarizations, P, to a threshold number.

The threshold number is equal to the number of depolarizations evaluated multiplied by the target paced percentage. Microprocessor 64 may calculate the threshold number using the values of these parameters. Alternatively, the threshold number may be a programmable parameter instead of, or in addition to, the target paced percentage. In this embodiment, the threshold number is seventy percent of twenty, or fourteen.

Alternatively, microprocessor 64 may compare the number of depolarizations classified as intrinsic among the most recent twenty depolarizations to a threshold number, which may be determined from a target intrinsic percentage parameter value, or may calculate a percentage of paced or intrinsic depolarizations and compare the percentage directly to the target paced percentage or target intrinsic percentage value.

Microprocessor determines if P is less than fourteen (154). If P is less than fourteen, the average intrinsic ventricular rate is greater than the pacing rate such that the ventricular rate is less stable than desired. In response to this determination, microprocessor 64 increases the pacing rate by decreasing the escape interval 130 (156). If microprocessor 64 determines that P is greater than fourteen (158), the pacing rate is higher than desired. In response to this determination, microprocessor 64 decreases the pacing rate by increasing the escape interval (160). If microprocessor 64 determines that P is equal to fourteen, the escape interval is not changed, and microprocessor 64 is directed to detect and classify another depolarization (142 and 144).

When the escape interval is adjusted, TC is set to zero (162). Setting TC to zero after adjusting the escape interval guarantees that at least ten cardiac cycles will occur between rate adjustments. During these ten cycles, microprocessor 64 continues to detect and classify the depolarizations.

Figure 8:
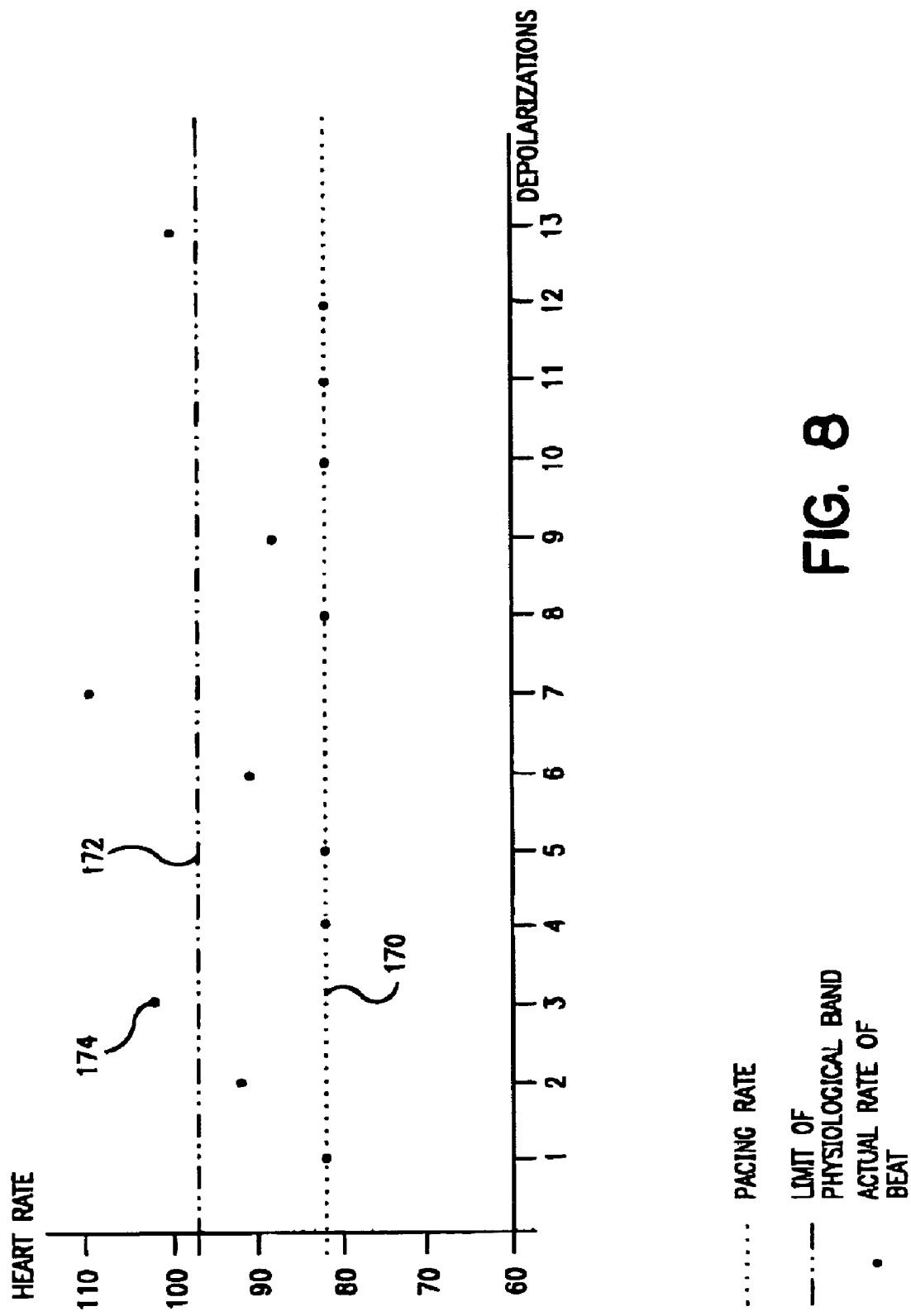
FIG. 8 is a timing diagram further illustrating an exemplary mode of operation of an implantable medical device to stabilize a ventricular rate as a function of measured R-R interval lengths and a depolarization rate or R-R interval length range.

FIG. 8 is a timing diagram further illustrating an alternative mode of operation of IMD 10 to stabilize a ventricular rate as a function of measured R-R interval lengths. In particular, the timing diagram is useful to illustrate techniques employed by IMD 10 to measure the ventricular rate stability as a function of measured R-R interval lengths.

The stability of the ventricular rate may be quantified by identifying the number of depolarizations that occur outside of a physiological band over a period of time. As shown in FIG. 8, the physiological band is a range of heart rates that is defined by the pacing rate 170 and a rate 172 above the pacing rate. In the example shown in FIG. 8, the physiological band includes rates from 82 beats-per-minute, which is the pacing rate, to 97 beats-per-minute.

Each ventricular depolarization 174 occurs at a rate that is inversely related to the R-R interval length for that depolarization 174. Microprocessor 64 may quantify the stability of the ventricular rate by identifying the number of depolarizations 174 that occur outside of the physiological band. Microprocessor 64 may detect the occurrence of and measure an R-R interval length for each depolarization 174 by any of the above-described methods. Microprocessor 64 may determine a rate for each depolarization 174 as a function of the measured R-R interval length, and compare the rate to the range of rates defined by the physiological band. Alternatively, microprocessor 64 may determine a range of R-R interval lengths corresponding to the physiological band rates, and may compare the measured R-R interval length to the R-R interval length range.

Figure 9:
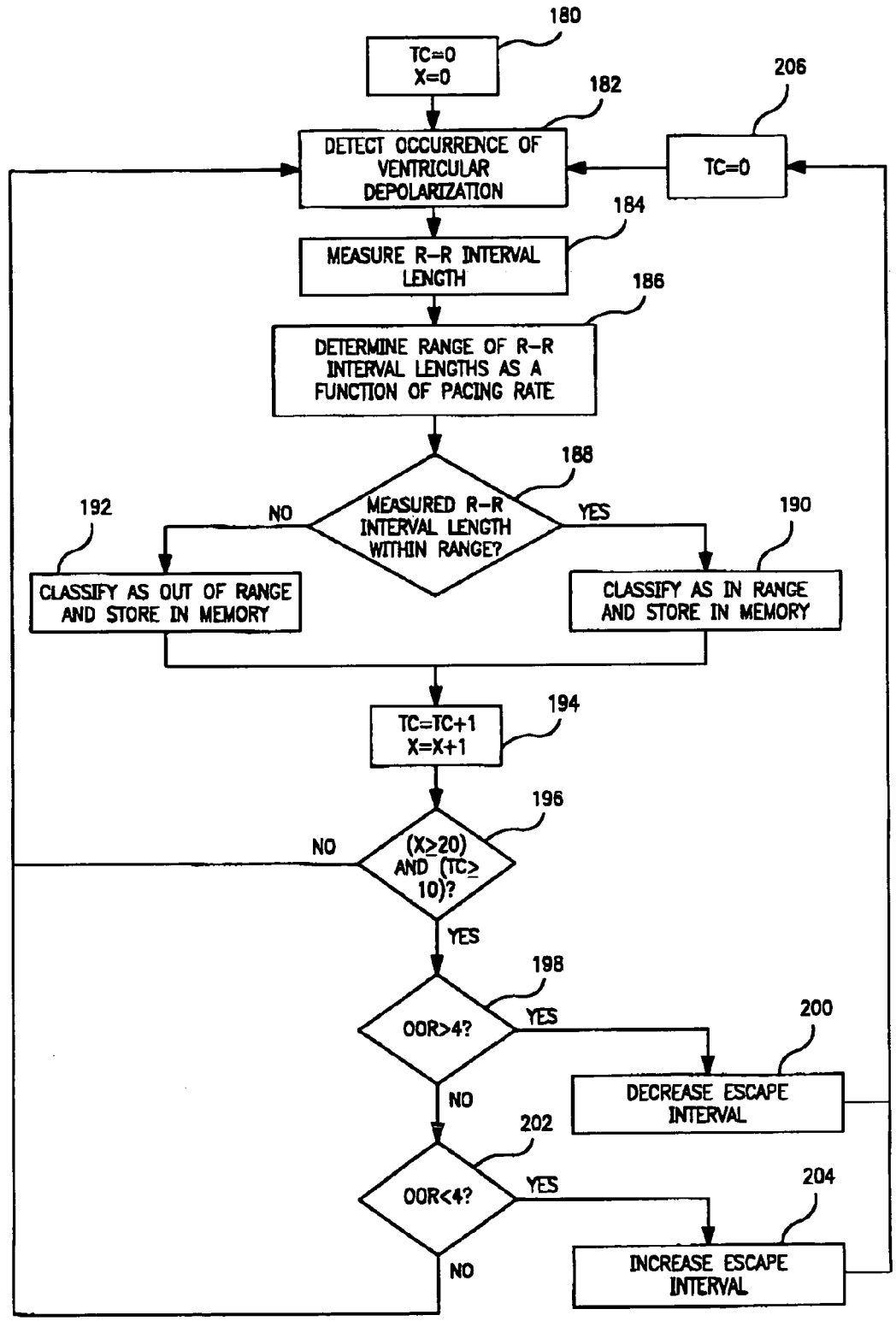
FIG. 9 is a flow diagram further illustrating the operation of an implantable medical device to stabilize a ventricular rate as a function of measured R-R interval lengths and an R-R interval length range.

FIG. 9 is a flow diagram further illustrating the operation of IMD 10 to stabilize a ventricular rate as a function of measured R-R interval lengths and an R-R interval length range. In particular, the flow diagram illustrates one embodiment of a ventricular rate stabilization algorithm that may be executed by microprocessor 64, which quantifies the stability of the ventricular rate by identifying the number of depolarizations, among a number of the most recently detected depolarizations, that have measured R-R interval lengths that are outside of a range of R-R interval lengths corresponding to a physiological band. Microprocessor 64 compares this number to a threshold value. If, by this comparison, the ventricular rate is found to be less stable then desired, microprocessor 64 may increase the pacing rate by decreasing the escape interval length in order to stabilize the ventricular rate. This algorithm may be executed, for example, during conducted atrial fibrillation.

In this exemplary embodiment, the target value for the percentage of depolarizations outside the range is set at twenty percent. Again, any percentage target value may be used, although it has been found that twenty percent of depolarizations outside the range correlates with desirable ventricular rate stability. Generally, the range from ten to thirty percent is preferred.

In this embodiment, microprocessor 64 determines whether and how to adjust the escape interval length based on the percentage of depolarizations that occurred at a rate outside of the physiological band, among a number of the most recently detected deopolarizations. The number of depolarizations considered may, for example, be twenty as shown in FIG. 7. Again, any number of depolarizations may be considered, but as mentioned above, the greater the number of depolarizations considered, the more resistant this ventricular rate stabilization algorithm is to overpacing caused by bursts of rapid ventricular depolarizations.

This embodiment of the ventricular rate stabilization algorithm also sets the time constant after the variation of the pacing rate at ten cycles, guaranteeing ten cardiac cycles between rate changes.

As was the case with the above embodiment, the target percentage, number of depolarizations considered, and the value of the time constant may be included in loaded software, or selected by a physician. The physician may select the values of these parameters using an external programming unit and/or RF transmitter and receiver telemetry unit 78. These values may be stored in at least one of RAM 68, or off-board circuit 62.

Once again, when this embodiment of the ventricular rate stabilization algorithm is initiated, it will need to evaluate twenty cardiac cycles before it can make its first determination of the percentage of depolarizations within the most recent twenty depolarizations which occurred at a rate outside of the physiological band. Thus, the value of an initialization iteration counter variable, X, is initially set at zero (180). The value of a time constant counter variable, TC, is also initially set to zero. The value of the escape interval may, for example, initially be set to a value corresponding to the minimum allowed pacing rate.

Each time that microprocessor 64 detects the occurrence of a ventricular depolarization (182), it measures the R-R interval length of the depolarization (184). Microprocessor 64 may detect the occurrence of a ventricular depolarization and measure the R-R interval length by any of the methods discussed above.

Microprocessor 64 may also determine a range of R-R interval lengths as a function of the current pacing rate (186). Microprocessor 64 may retrieve the current pacing rate from memory, such as RAM 68 or off-board circuit 62, or may calculate the current pacing rate as a function of the current escape interval. The value of the upper rate of the physiological band may be included in loaded software, or selected by a physician. Alternatively, the upper rate may be defined by the software or physician as a rate a certain number of beats-per-minute above the current pacing rate, or as a rate a certain percentage of the current pacing rate greater than the current pacing rate. Microprocessor 64 may determine the range of R-R interval lengths as a function of the current pacing rate and the upper rate of the physiological band.

Microprocessor 64 may compare the measured R-R interval length of a detected ventricular depolarization to the determined range of R-R interval lengths in order to determine if the measured R-R interval length falls within the range (188). If microprocessor 64 determines that the measured R-R interval length falls within the range, it may classify the depolarization as in range and store an indication that the depolarization was in range in memory (190), such as RAM 68 or off-board circuit 62. If microprocessor 64 determines that the measured R-R interval length falls outside of the range, it may classify the depolarization as out of range and store an indication that the depolarization was out of range in memory (192), such as RAM 68 or off-board circuit 62.

Each time microprocessor 64 classifies a depolarization, the values of X and TC are incremented by one (194). Until the value of X equals or exceeds twenty and the value of TC equals or exceeds ten, microprocessor 64 may not proceed to determine the percentage of out of range depolarizations among the most recently detected twenty depolarizations (196). Thus, during the initialization period, microprocessor 64 is directed to measure and classify twenty R-R intervals before any determination or escape interval adjustment is made.

After an adequate number of R-R intervals have been measured and classified, in this case twenty, microprocessor 64 proceeds to compare the percentage of out of range depolarizations to the target percentage. Microprocessor 64 may make this comparison, as illustrated in this embodiment, by comparing the number of depolarizations, among the most recent twenty depolarizations, whose measured R-R interval length was classified as out of range, to a threshold number. The number of the most recent twenty depolarizations is represented in this embodiment by the variable out of range (OOR).

The threshold number is equal to the number of depolarizations evaluated multiplied by the target out of range percentage. Microprocessor 64 may calculate the threshold number using the values of these parameters. Alternatively, the threshold number may be a programmable parameter instead of, or in addition to, the target paced percentage. In this exemplary embodiment, the threshold number is twenty percent of twenty, or four.

Alternatively, microprocessor 64 may compare the number of depolarizations classified as in range among the most recent twenty depolarizations to a threshold number, which may be determined from a target in range percentage parameter value, or may calculate a percentage of out of range or in range depolarizations and compare the percentage directly to the target out of range percentage or target in range percentage value.

Microprocessor determines if OOR is greater than four (198). If OOR is greater than four, the average intrinsic ventricular rate is greater than the pacing rate such that the ventricular rate is less stable than desired. In response to this determination, microprocessor 64 increases the pacing rate by decreasing the escape interval 130 (200). If microprocessor 64 determines that OOR is greater than four (202), the pacing rate is higher than desired. In response to this determination, microprocessor 64 decreases the pacing rate by increasing the escape interval (204). If microprocessor 64 determines that OOR is equal to four, the escape interval is not changed, and microprocessor 64 is directed to measure and classify another depolarization (182–188).

When the escape interval is adjusted, TC is set to zero (206). Setting TC to zero after adjusting the escape interval guarantees that at least ten cardiac cycles will occur between rate adjustments. During these ten cycles, microprocessor 64 continues to measure and classify the depolarizations.

Figure 10:
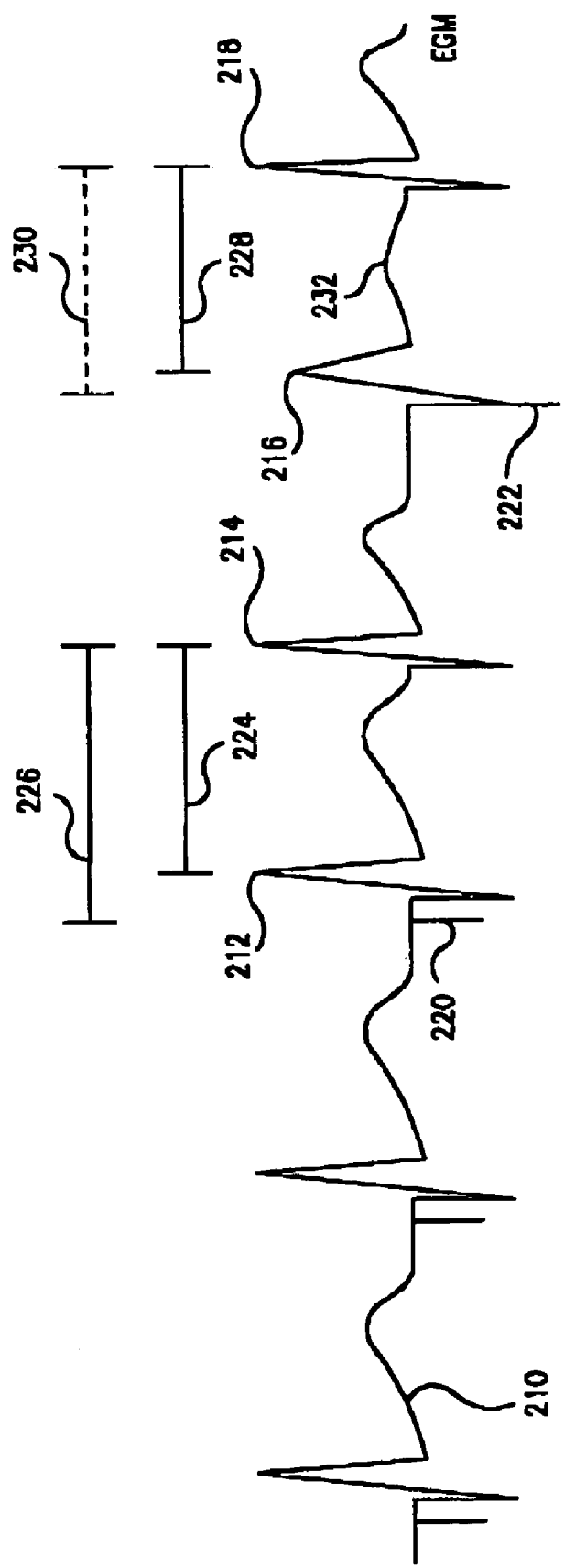
FIG. 10 is a timing diagram providing an overview of exemplary modes of operation of an implantable medical device to identify compensatory pauses and to stabilize a ventricular rate as a function of measured lengths of the compensatory pauses.

FIG. 10 is a timing diagram providing an overview of exemplary modes of operation of IMD 10 to identify compensatory pauses and to stabilize a ventricular rate as a function of measured lengths of the compensatory pauses, in accordance with another embodiment. In particular, the timing diagram is useful to illustrate techniques employed by IMD 10 to identify an R-R interval as a compensatory pause, and to measure the length of the compensatory pause.

As was the case with EGM signal 100 of FIG. 6, EGM signal 210 represents a signal received from electrodes 28 and 29 on lead 18 of IMD 10. EGM signal 210 represents the electrical activity sensed by electrodes 28 and 29 within a ventricle of heart 8. R-waves 212–218 of EGM signal 210, which represent depolarizations of the ventricle, are shown. Pacing pulses 220 and 222 are also shown on EGM signal 210.

Microprocessor 64 may identify a compensatory pause by identifying an intrinsic ventricular depolarization that occurs after a paced ventricular depolarization. For example, microprocessor 64 may detect the occurrence of the ventricular depolarizations associated with R-waves 212 and 214, and determine whether each depolarization was caused by a pacing pulse or intrinsic. Microprocessor 64 may detect the occurrence of the depolarizations and make the determination by any of the above-discussed methods. Because pacing pulse 220 was delivered before the depolarization associated with R-wave 212 occurred, microprocessor 64 will determine that the depolarization was cause by pacing pulse 220 using the above-discussed methods. Because no pacing pulse was delivered before the depolarization associated with R-wave 214, microprocessor 64 will determine that the depolarization was intrinsic. Thus, microprocessor 64 will identify the interval 224 between R-wave 212 and R-wave 214 as a compensatory pause. Alternatively, if a ventricular blanking period is utilized, microprocessor 64 may identify the interval 226 between pacing pulse 220 and R-wave 214 as the compensatory pause.

Using the above-discussed methods for identifying the occurrence of a ventricular depolarization and determining whether the depolarization was caused by a pacing pulse or was intrinsic, microprocessor 64 might also classify interval 228 or 230 as a compensatory pause due to the delivery of pacing pulse 222. Interval 228 or 230 is not a compensatory pause because the depolarization associated with R-wave 216 was not caused by pacing pulse 222, but was instead an intrinsic ventricular depolarization that occurred nearly simultaneously with the delivery of pacing pulse 222. Thus, interval 228 or 230 is not a compensatory pause because the intrinsic depolarization associated with R-wave 218 does not follow a depolarization caused by a pacing pulse.

The depolarization associated with R-wave 216 is a fusion beat. As discussed above, fusion beats can result in magnification, diminishment or abolition of the R-wave. R-wave 216 is showed as diminished relative to the other R-waves of signal 210. Fusion beats also result in the diminishment of the T-wave. T-wave 232 is shown diminished relative to the other T-waves of signal 210.

In order to correctly identify compensatory pauses, microprocessor 64 may discriminate between depolarizations caused by pacing pulses and fusion beats. EGM amplifier 94 provides an amplified version of electrogram signal 210 to digital controller/timer circuit 74. ADC and multiplexer unit 84 may digitize the electrogram signal received by circuit 74, and the digitized electrogram signal may be received by microprocessor 64 via data communications bus 72. Microprocessor 64 may utilize digital signal processing techniques known in the art to identify T-waves within the digitized electrogram signal and measure the amplitude of the T-waves. Microprocessor 64 may compare the amplitudes of the identified T-waves to a threshold value in order to identify fusion beats. The threshold value may be may be included in loaded software, or selected by a physician and stored in memory as described above. If microprocessor 64 would have otherwise identified an occurrence of a depolarization caused by a pacing pulse by the above-described methods, microprocessor 64 will identify the depolarization as a fusion beat if the amplitude of the T-wave does not exceed the threshold value.

Alternatively, IMD 10 may include a circuit (not shown in FIGS. 3 and 5) that identifies the occurrence of T-waves in an electrogram signal as a function of the threshold value. The circuit may generate a signal when the T-wave occurrence is identified, which may be received by microprocessor 64. If microprocessor 64 would have otherwise identified an occurrence of a depolarization caused by a pacing pulse by the above-described methods, microprocessor 64 will identify the depolarization as a fusion beat if it does not receive a T-wave occurrence signal from the circuit.

Figure 11A:
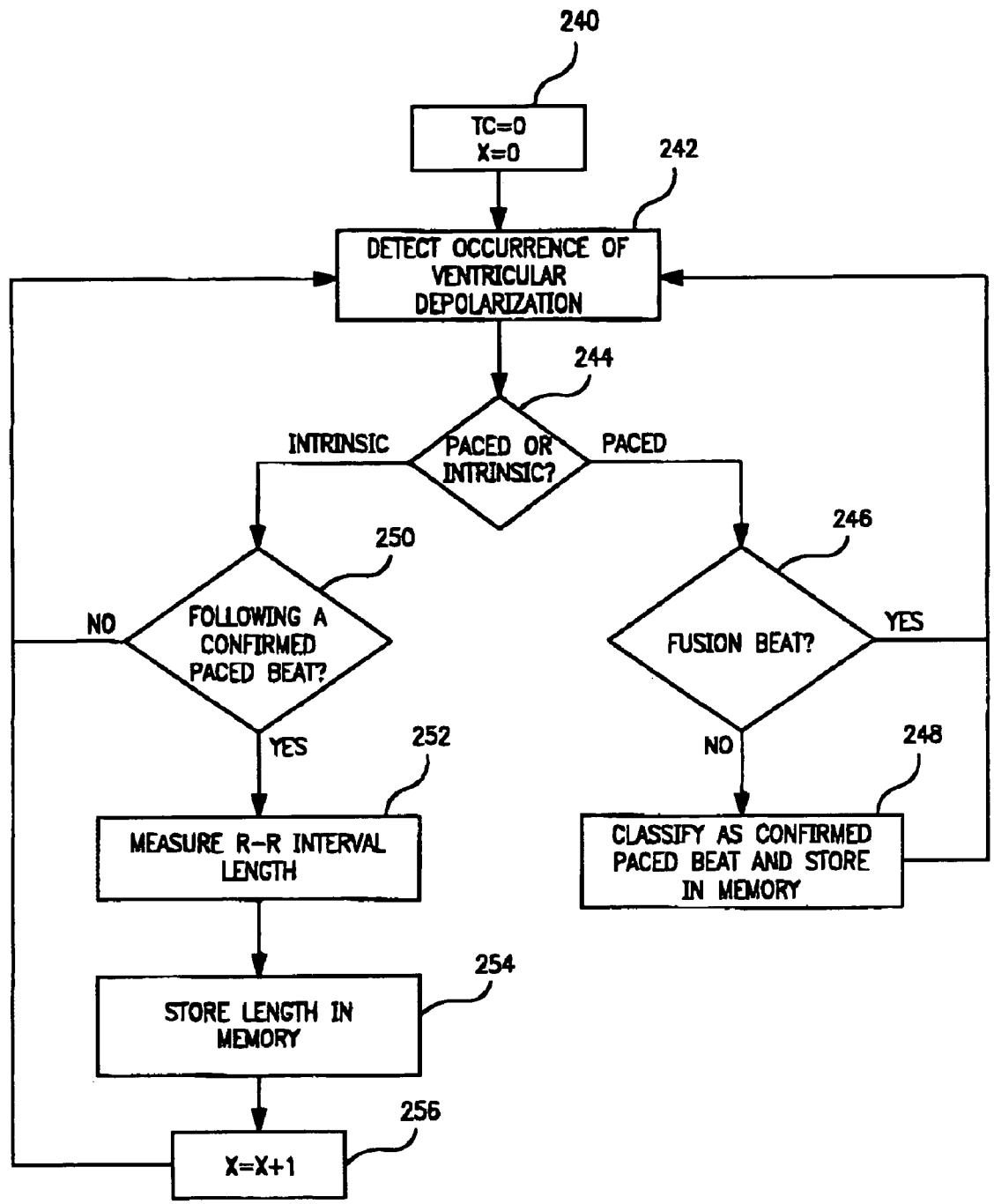
FIG. 11A is a flow diagram further illustrating the operation of an implantable medical device to identify compensatory pauses and measure the lengths of the compensatory pauses.

FIG. 11A is a flow diagram further illustrating the operation of IMD 10 to identify compensatory pauses and measure the lengths of the compensatory pauses. The flow diagram illustrates one functional subdivision of an embodiment of a ventricular rate stabilization algorithm that may be executed by microprocessor 64, which identifies compensatory pauses, measures the length of the compensatory pauses, and stabilizes the ventricular rate by adjusting the escape interval as a function the average of recently measured compensatory pause lengths. This algorithm stabilizes the ventricular rate by adjusting the escape interval to maintain it at or near the average length of a compensatory pause. This algorithm may be executed, for example, during conducted atrial fibrillation.

In this embodiment, microprocessor 64 determines whether and how to adjust the escape interval length based on average of the most recent ten compensatory pauses measured, which may be referred to as the mean compensatory pause (MCP). Any number of compensatory pauses may be considered, but the greater the number of compensatory pauses considered, the more resistant this ventricular rate stabilization algorithm is to overpacing caused by bursts of rapid ventricular depolarizations.

In this exemplary embodiment, the target value for the escape interval is set at the MCP minus ten milliseconds. Again, any target value may be used, although it has been found that values within ten milliseconds of the MCP successfully stabilize the intrinsic ventricular rate without detrimentally increasing the mean ventricular rate.

This embodiment of the ventricular rate stabilization algorithm also sets the time constant after the variation of the pacing rate at ten cycles, guaranteeing ten cardiac cycles between rate changes.

As was the case with the above embodiments, the target value for the escape interval, number of compensatory pauses considered, and the value of the time constant may be included in loaded software, or selected by a physician. The physician may select the values of these parameters using an external programming unit and/or RF transmitter and receiver telemetry unit 78. These values may be stored in at least one of RAM 68, or off-board circuit 62.

When this embodiment of the ventricular rate stabilization algorithm is initiated, it will need to evaluate ten cardiac cycles before it can first compare the current escape interval to the target value. Thus, the value of an initialization iteration counter variable, X, is initially set at zero (240). The value of a time constant counter variable, TC, is also initially set to zero. The value of the escape interval may, for example, initially be set to a value corresponding to the minimum allowed pacing rate.

Each time that microprocessor 64 detects the occurrence of a ventricular depolarization (242), it determines whether the depolarization was caused by a pacing pulse or was intrinsic (244). Microprocessor 64 may detect the occurrence of a ventricular depolarization and make this determination by any of the methods discussed above.

If microprocessor 64 initially determines that the depolarization was caused by a pacing pulse, it determines whether the depolarization was the result of a fusion beat (246). Microprocessor 64 may make this determination using any of the above-described methods. If microprocessor 64 determines that the depolarization was not a fusion beat, it classifies the depolarization as a confirmed paced beat (248), stores an indication that the depolarization was a confirmed paced beat in memory, and waits to detect the next occurrence of a depolarization. If microprocessor 64 determines that the depolarization was a fusion beat, it waits to detect the next occurrence of a depolarization.

If microprocessor 64 determines that the depolarization was intrinsic, it further determines whether the intrinsic depolarization followed a confirmed paced beat (250). If microprocessor 64 determines that the intrinsic depolarization followed a confirmed paced beat, it measures the length of the R-R interval associated with the intrinsic depolarization (252). Microprocessor 64 may measure the R-R interval by any of the above-described methods. Microprocessor 64 stores the length of the R-R interval, which is a compensatory pause length, in memory (254), and increments the value of X by one (256).

Figure 11B:
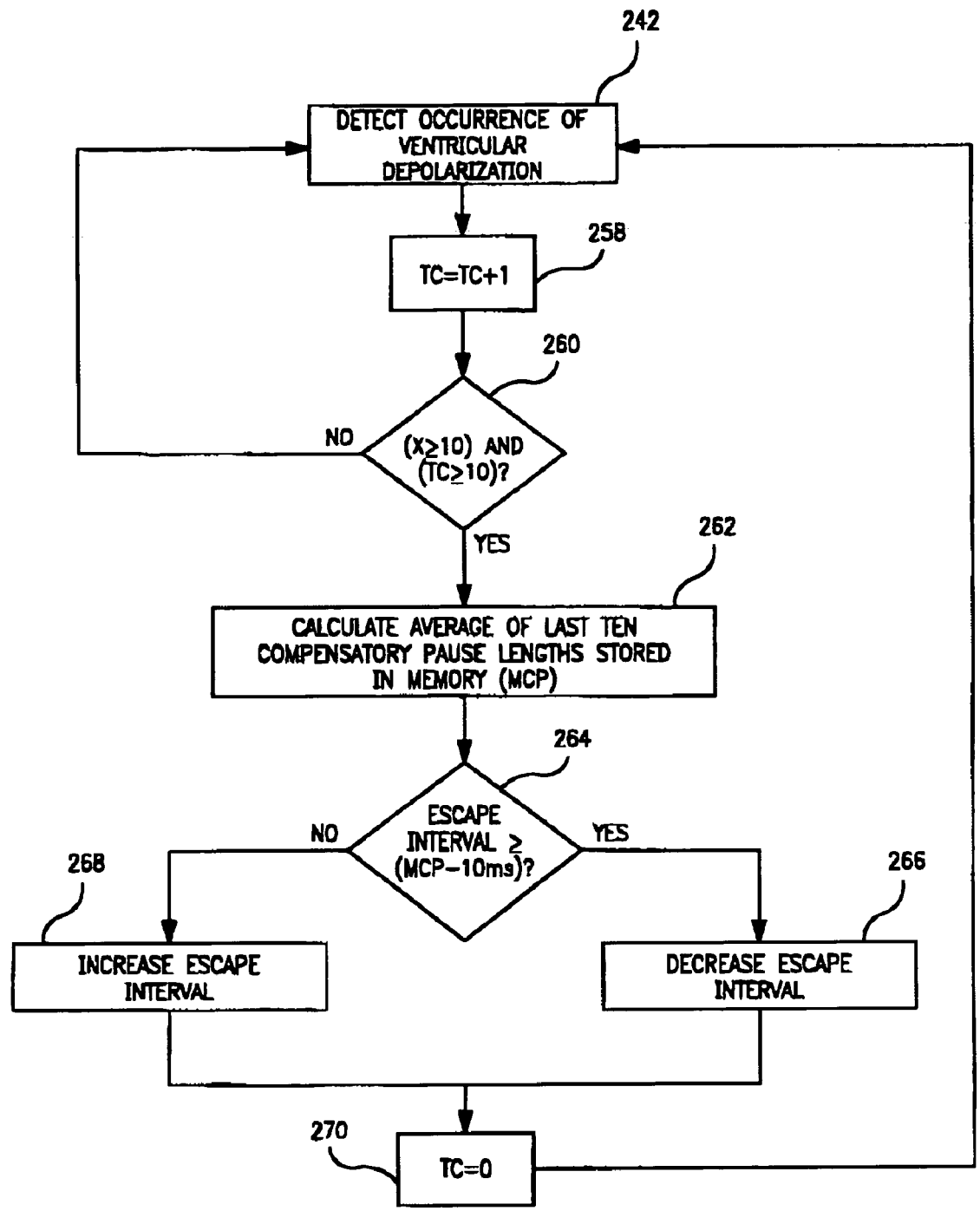
FIG. 11B is a flow diagram further illustrating the operation of an implantable medical device to stabilize a ventricular rate as a function of measured lengths of the compensatory pauses.

FIG. 11B is a flow diagram further illustrating the operation of an implantable medical device to stabilize a ventricular rate as a function of measured lengths of the compensatory pauses. The flow diagram illustrates a second functional subdivision of an embodiment of a ventricular rate stabilization algorithm that may be executed by microprocessor 64, which identifies compensatory pauses, measures the length of the compensatory pauses, and stabilizes the ventricular rate by adjusting the escape interval as a function of the average of recently measured compensatory pause lengths.

Again, as shown in FIG. 11A, each time microprocessor 64 stores a compensatory pause length in memory, the value of X is incremented by one (256). Each time microprocessor 64 detects the occurrence of a ventricular depolarization, the value of TC is incremented by one (258), as shown in FIG. 11B. Until the values of X and TC equal or exceeds ten, microprocessor 64 may not proceed to compare the current escape interval to the target value (260). Thus, during the initialization period, microprocessor 64 is directed to detect and measure ten compensatory pauses before any comparison or escape interval adjustment is made.

As shown in FIG. 11B, after at least ten compensatory pauses have been measured and classified, microprocessor 64 proceeds to calculate the average of the ten most recently measured compensatory pause lengths, which may be referred to as the mean compensatory pause, or MCP (262). Microprocessor 64 compares the current escape interval to the target value, which is MCP minus a time second, e.g., ten milliseconds (264). If the current value of the escape interval is greater than or equal to the target value, the escape interval is decreased (266). If the current value of the escape interval is less than the target value, the escape interval is increased (268). In this manner, microprocessor 64 maintains the escape interval at or near MCP minus ten milliseconds, which has been shown to successfully stabilize the intrinsic ventricular rate without detrimentally increasing the mean ventricular rate.

When the escape interval is adjusted, TC is set to zero (270). Setting TC to zero after adjusting the escape interval guarantees that at least ten cardiac cycles will occur between rate adjustments. During these ten cycles, microprocessor 64 continues to measure and classify the depolarizations.

The escape interval may be increased or decreased (156, 160, 200, 204, 266, or 268 of FIGS. 7, 9 and 11B) as indicated by the result of a comparison in a variety of ways. In some embodiments, for example, the escape interval could be increased or decreased by a fixed amount, such as five beats-per-minute. In other embodiments, the escape interval could be increased by one amount, and decreased by a second amount. In still other embodiments, the amount by which the escape interval is to be increased or decreased could be determined as a function of a result of the comparison.

The amount of increase or decrease could, for example, be determined as a function of the difference between the number of depolarizations that were the result of a pacing pulse or whose R-R interval length was out of range on one hand, and the threshold value on the other. The relationship between this difference and the amount of increase or decrease could be described by an equation that defines a curve or line. The values or equations could be included in loaded software, or selected by a physician and stored in memory as described above. With respect to the increase or decrease of the escape interval as a function of the compensatory pause (266 and 268 of FIG. 11B), the escape interval could simply be set at the target value, which in that embodiment was MCP minus ten milliseconds, after each new calculation of MCP (264).

Additionally, the adjustment of the escape interval could occur over one cardiac cycle, or could occur gradually during the length of the time constant after variation of the pacing rate.

The invention further includes within its scope the methods of making and using the systems described above. These methods are not limited to the specific examples described above, but may be adapted to meet the needs of a particular patient. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. A method comprising:
   detecting an occurrence of a depolarization within a ventricle;
   measuring an R-R interval length for the depolarization determining a range of R-R interval lengths;
   determining whether the R-R interval length falls within the range of R-R interval lengths as a function of a pacing rate; and
   adjusting an escape interval as a function of the determination wherein determining the range comprises determining a physiological maximum rate as a function of the pacing rate and identifying a range of R-R interval lengths from a first R-R interval length corresponding to the physiological maximum rate to a second R-R interval length corresponding to the pacing rate.

2. The method of claim 1 wherein determining the physiological maximum rate comprises adding a physiological band value to the pacing rate.

3. The method of claim 1, wherein adjusting the escape interval comprises adjusting the escape interval based on a difference between the R-R interval length measured and an R-R interval length of the range.

4. A method comprising:
   measuring a length of each of a plurality of compensatory pauses;
   calculating an average length as a function of the lengths of the measured compensatory pauses;
   comparing the average length to an escape interval; and
   adjusting the escape interval as a function of the comparison.

5. The method of claim 4, wherein measuring the length of a compensatory pause comprises:
   detecting occurrences of depolarizations within a ventricle;
   identifying an intrinsic ventricular depolarization;
   determining whether a preceding depolarization that preceded the intrinsic ventricular depolarization was caused by a pacing pulse; and
   measuring a length of an interval from a time of the preceding depolarization to a time of the intrinsic ventricular depolarization based on the determination.

6. The method of claim 5, wherein determining whether the preceding depolarization was caused by a pacing pulse comprises:

determining whether a pacing pulse was delivered to the ventricle prior to the preceding depolarization;
sensing a T-wave that occurs after the depolarization; and
analyzing the T-wave, wherein measuring the length of the interval comprises measuring the length of the interval based on the determination and the analysis.

7. The method of claim 6, wherein analyzing the T-wave comprises:

measuring an amplitude of the T-wave; and comparing the amplitude to a threshold value.

8. The method of claim 4, wherein calculating the average length comprises calculating the average of the lengths of a subset of the plurality.

9. The method of claim 4, wherein calculating the average length comprises calculating the average of the ten most recently measured lengths.

10. An implantable medical device comprising:

an electrode to sense electrical activity within a ventricle; and
a processor to detect occurrences of a plurality of depolarizations of the ventricle as a function of the electrical activity, to measure an R-R interval length of a depolarization, to determine whether the R-R interval length falls within a range of R-R interval lengths, and to adjust an escape interval as a function of the determination, wherein the range comprises R-R interval lengths from a first R-R interval length corresponding to a pacing rate to a second R-R interval length corresponding to a physiological maximum rate that is a physiological band value greater than the pacing rate.

11. A computer-readable medium comprising instructions that cause a processor to:

receive signals indicating occurrences of a plurality of depolarizations of a ventricle;
measure a length of each of a plurality of compensatory pauses as a function of the signals;
calculate an average length as a function of the lengths of the measured compensatory pauses;
compare the average length to an escape interval; and
adjust the escape interval as a function of the comparison.

12. The computer-readable medium of claim 11, wherein the instructions that cause a processor to measure the length of a compensatory pause further comprise instructions that cause a processor to:

identify an intrinsic ventricular depolarization;
determine whether a preceding depolarization that preceded the intrinsic ventricular depolarization was caused by a pacing pulse delivered to the ventricle; and
measure a length of an interval from a time of the preceding depolarization to a time of the intrinsic ventricular depolarization based on the determination.

13. An implantable medical device comprising:

means to detect occurrences of a plurality of depolarizations within a ventricle;
means to measure a length of each of a plurality of compensatory pauses as a function of the depolarizations;
means to calculate an average length as a function of the lengths of the measured compensatory pauses;
means to compare the average length to an escape interval; and
means to adjust the escape interval as a function of the comparison.

14. The implantable medical device of claim 13, wherein the means to measure the length of compensatory pauses further comprises:

means to identify an intrinsic ventricular depolarization;
means to determine whether a preceding depolarization that preceded the intrinsic ventricular depolarization was caused by a pacing pulse delivered to the ventricle; and
means to measure a length of an interval from a time of the preceding depolarization to a time of the intrinsic ventricular depolarization based on the determination.

* * * * *